US012667832B2

(12) United States Patent
Hung et al.

(10) Patent No.: US 12,667,832 B2
(45) Date of Patent: Jun. 30, 2026

(54) CATALYSTS AND THEIR USES IN ONE-POT DIASTEREOSELECTIVE SYNTHESIS OF REMDESIVIR

(71) Applicant: Academia Sinica, Taipei (TW)

(72) Inventors: Shang-Cheng Hung, Taipei City (TW); Chi-Huey Wong, Taipei City (TW); Veeranjaneyulu Gannedi, Taipei (TW); Bharath Kumar Villuri, Taipei (TW); Nimmakayala Sivakumar Reddy, Taipei (TW); Chiao-Chu Ku, Taipei City (TW)

(73) Assignee: Academia Sinica, Taipei (TW)

( * ) Notice: Subject to any disclaimer, the term of this patent is extended or adjusted under 35 U.S.C. 154(b) by 540 days.

(21) Appl. No.: 18/030,773

(22) PCT Filed: Oct. 7, 2021

(86) PCT No.: PCT/US2021/053886

§ 371 (c)(1),
(2) Date: Apr. 7, 2023

(87) PCT Pub. No.: WO2022/076638

PCT Pub. Date: Apr. 14, 2022

(65) Prior Publication Data

US 2023/0381761 A1 Nov. 30, 2023

Related U.S. Application Data

(60) Provisional application No. 63/089,028, filed on Oct. 8, 2020.

(51) Int. Cl.
*B01J 31/02* (2006.01)
*C07H 1/02* (2006.01)
*C07H 7/06* (2006.01)

(52) U.S. Cl.
CPC ............ *B01J 31/0245* (2013.01); *C07H 1/02* (2013.01); *C07H 7/06* (2013.01)

(58) Field of Classification Search
None
See application file for complete search history.

(56) References Cited

U.S. PATENT DOCUMENTS

2017/0226146 A1* 8/2017 Chung .................... C07H 1/00

* cited by examiner

*Primary Examiner* — Yun Qian
(74) *Attorney, Agent, or Firm* — NZ Carr Law Office

(57) ABSTRACT

Disclosed herein are novel catalysts for producing remdesivir in one-pot manner, in which a diastereomerically enriched form of an intermediate, which following acidic hydrolysis would give rise to the desired remdesivir, was produced with the aid of the disclosed novel catalysts. Also disclosed herein is an improved process for the preparation of remdesivir without the need to separate one of the enantiomers while minimizing the formation of undesired isomers, thus offers economic advantages for operation on a commercial scale.

1 Claim, 2 Drawing Sheets

1 (remdesivir, GS-5734)

CATALYSTS AND THEIR USES IN ONE-POT DIASTEREOSELECTIVE SYNTHESIS OF REMDESIVIR

CROSS-REFERENCES TO RELATED APPLICATIONS

This application claims priority and the benefit of U.S. Provisional Patent Application No. 63/089,028, filed Oct. 8, 2020, the entirety of which is incorporated herein by reference.

BACKGROUND OF THE INVENTION

1. Field of the Invention

The present disclosure relates to a diastereoselective synthetic process for the preparation of remdesivir (or GS-5734). More particularly, the disclosure invention relates to a one-pot process for diastereoselective synthesis of remdesivir carried out in the presence of a chiral imidazo-cinnamaldehyde-derived carbamate catalyst.

2. Description of Related Art

Remdesivir 1 (GS-5734, FIG. 1) is a broad-spectrum antiviral compound that has been developed by Gilead Sciences for hepatitis C virus and Ebola virus. Remdesivir 1 is a prodrug of nucleotide (ProTide) with high cell permeability and is a promising therapeutic agent against Severe Acute Respiratory Syndrome (SARS), Middle East respiratory syndrome (MERS), and SARS Coronavirus 2 (SARS-CoV-2). It metabolizes inside the host cell to the corresponding nucleotide triphosphate (NTP) and targets the RdRp enzyme to inhibit viral replication and translation within the cell. On a molecular level, the (S)-P-1 plays a crucial role in comparison with its (R)-P-isomer with respect to its potency, toxicity, rate of metabolism, and phosphorylation in vivo.

The preparation of remdesvir 1 has been explored by Gilead's team. The entire procedure resulted in attributing a high price—$2,340 US dollars for a 5-day course per person in clinic, announced by Gilead on 29 Jun. 2020. Gilead's process is presented in FIG. 2, the key step of (S)-P-phosphoamidation requires high diastereomeric purity at the phosphorus center. Coupling of 2-ethylbutyl-L-alanine 2 with $PO(OPh)Cl_2$ 3 in $Et_3N$ and $CH_2Cl_2$ yielded the phosphoramidoyl chloridate 4, which was directly treated with p-nitrophenol in one pot to give the 1/1 mixture of diastereomers 5 (80%) after column chromatography purification. The diastereomeric mixture 5 was initially separated by HPLC chiral column to deliver a small amount of optically pure solid 6, which was used as a seed for further resolution of 5 through selective crystallization in diisopropyl ether several times to furnish 6 in 39% yield. Coupling of 6 with the D-ribose-derived 5-alcohol 7 in the presence of $MgCl_2$ and diidopropylethylamine afforded the (S)-P-phosphoamidate 8 (70%), which underwent acidic cleavage of the isopropylidene group in 8 to provide remdesivir 1 (69%). Some drawbacks are concerned with the aforementioned synthetic route, including (1) an additional nucleophile, such as p-nitrophenol, should be employed for stabilization of the phosphoramidoyl chloridate 4; (2) the corresponding diastereomeric mixture 5 has to be purified by silica gel column chromatography before crystallization; (3) multiple crystallization steps of the 1/1 diastereomeric mixture 5 are necessary to isolate the desired pure diastereomer 6, which leads to a significant wastage of the rest materials (61%); (4) the products require purification by column chromatography in the last two steps, respectively; and (5) the overall yield for the last two steps is 48.3%, which may not be considered economic-friendly.

In view of the above, there exists in this art a need of an improved process for diastereoselective synthesis of remdesivir.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In accordance with a first aspect of this invention, there is provided novel catalysts for the synthesis of the anti-coronavirus drug remdesivir (or GS-5734) by producing a diastereomerically enriched form of compound 8, which is a (Sp)-diasteroisomer.

According to some embodiments of the present disclosure, the catalyst has the structure of formula (1), (1)

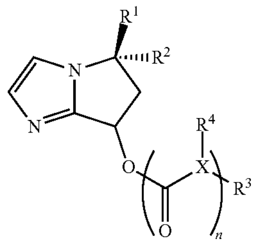

wherein,

X is C or N;

n is 0 or 1;

$R^1$ and $R^2$ are independently hydrogen or phenyl;

$R^3$ is tert-butyl, tert-butyldimethylsilyl (TBDMS), phenyl, benzyl, or adamantanyl; and $R^4$ is hydrogen provided that X is N, or $R^4$ is —$OCOCH_3$ provided that X is C.

The catalyst of formula (1) may be any one of,

26

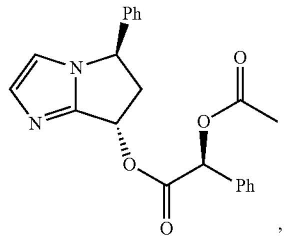

,

-continued
26A
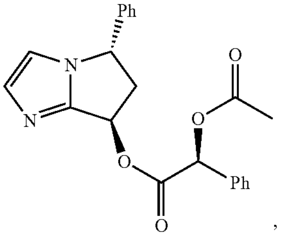
,
29
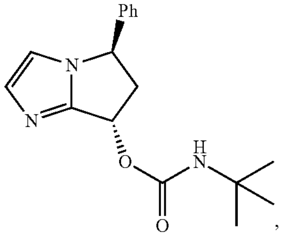
,
30
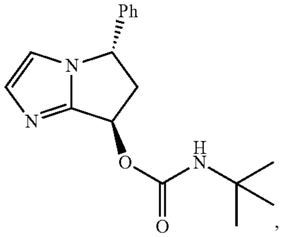
,
31
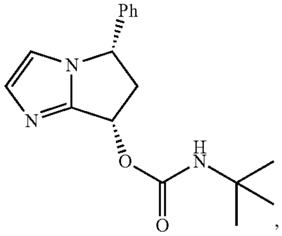
,
32
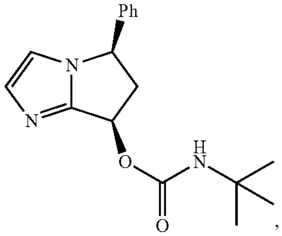
,
40
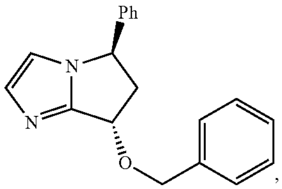
,
41
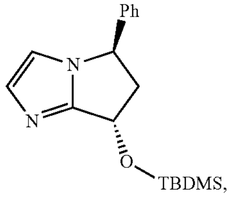
or
-continued
42
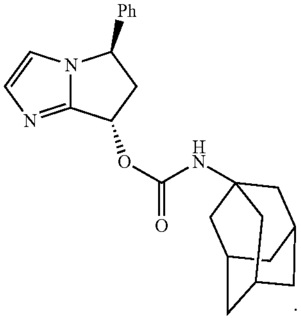
.
According to other embodiments of the present disclosure, the catalyst has the structure of formula (2-1)
(2-1)
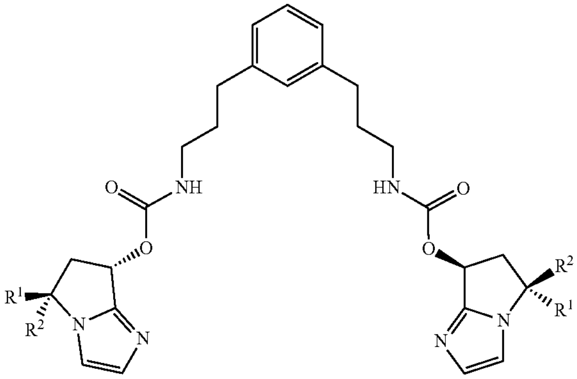
wherein, $R^1$ and $R^2$ are independently hydrogen or phenyl.
The catalyst of formula (2-1) may be any one of,
34
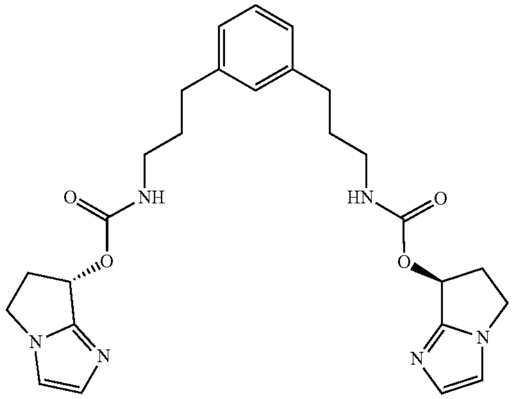

-continued

36

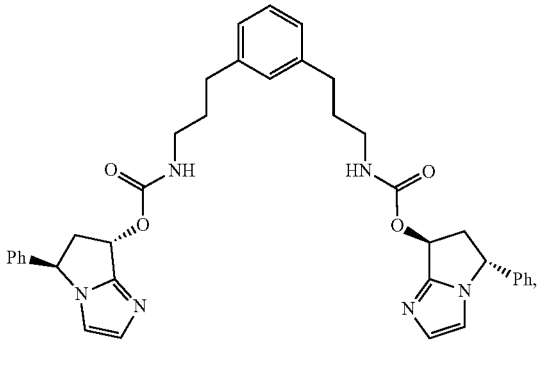

or

38

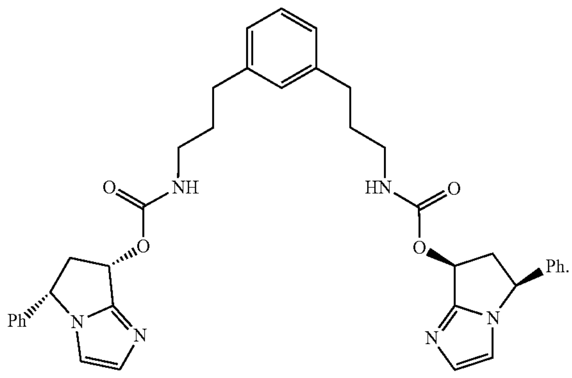

According to further embodiments of the present disclosure, the catalyst has the structure of formula (2-2), (2-2)

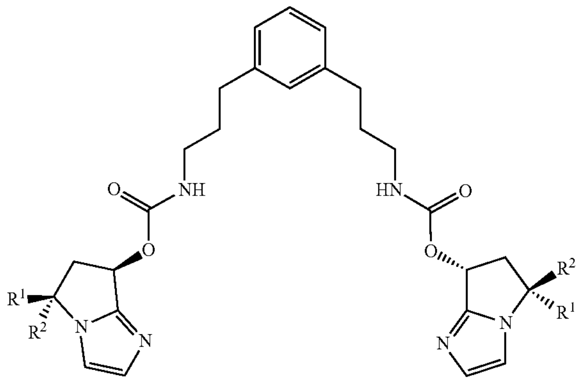

wherein, $R^1$ and $R^2$ are independently hydrogen or phenyl.

The catalyst of formula (2-2) may be any one of,

37

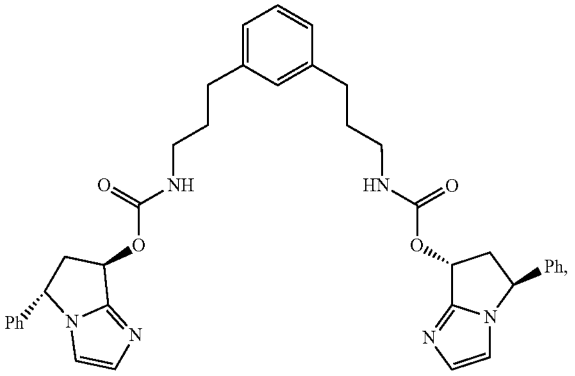

or

39

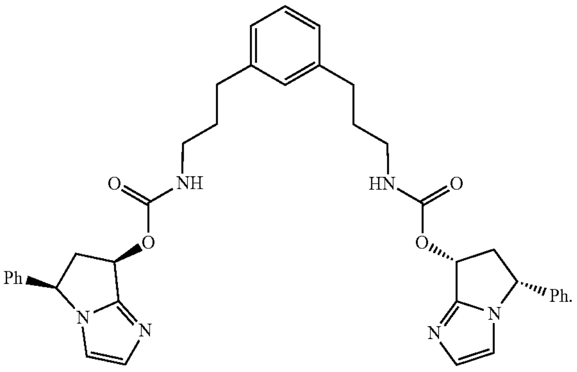

In accordance with a second aspect of this invention, there is provided a one-pot synthetic process for the preparation of remdesivir, the process comprises:

(a) diastereoselective coupling of compounds 4 and 7 in the presence of a catalyst of the present disclosure, thereby forming compound 8 with at least 85% selectivity; and (b) subjecting the compound 8 to acidic cleavage to give the remdesivir;

4

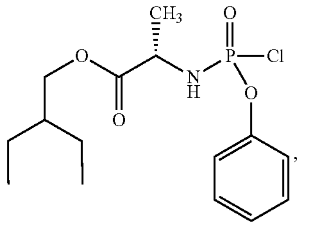

7

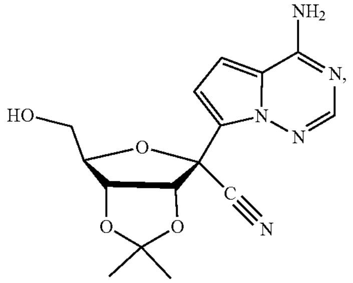

-continued

8

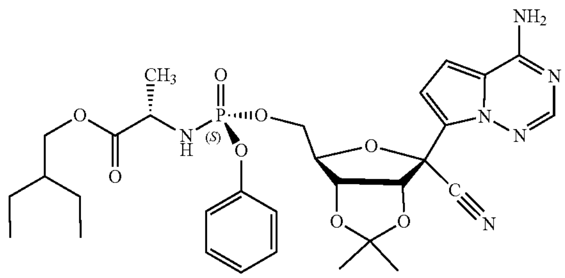

wherein, the compound 4 in the step (a) exists in a racemic mixture; and the steps (a) and (b) are performed in the same vessel without intermediate purification.

According to embodiments of the present disclosure, in the step (a), the catalyst is present in the amount of 10-100 mol % in the reaction mixture; and the reaction is performed at a temperature between −10° C. to −50° C. for a period of 12 to 48 h. Preferably, the catalyst is present in the amount of 20 mol % in the reaction mixture; and the reaction is performed at −20° C. for 24 h and the compound 8 is formed with at least 96% selectivity According to embodiments of the present disclosure, the step (b) is performed in an acidic solution that comprises p-toluenesulfonic acid (p-TSA) and methanol at a temperature between 20° C. to 60° C. for a period of 4-36 h. Preferably, the step (b) is performed at room temperature for 24 h.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The singular forms "a", "and", and "the" are used herein to include plural referents unless the context clearly dictates otherwise.

Figure 1:
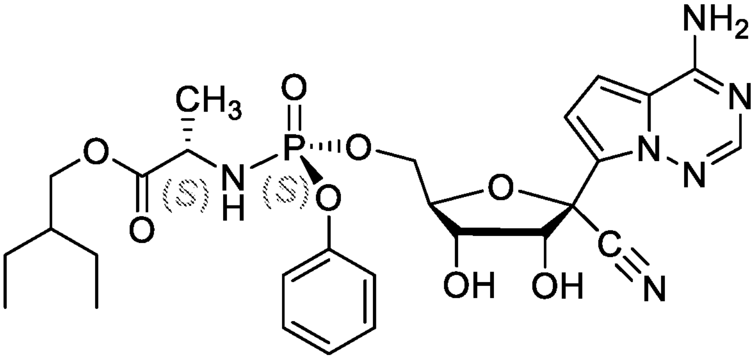
FIG. 1 depicts the structure of remdesivir.
Figure 2:
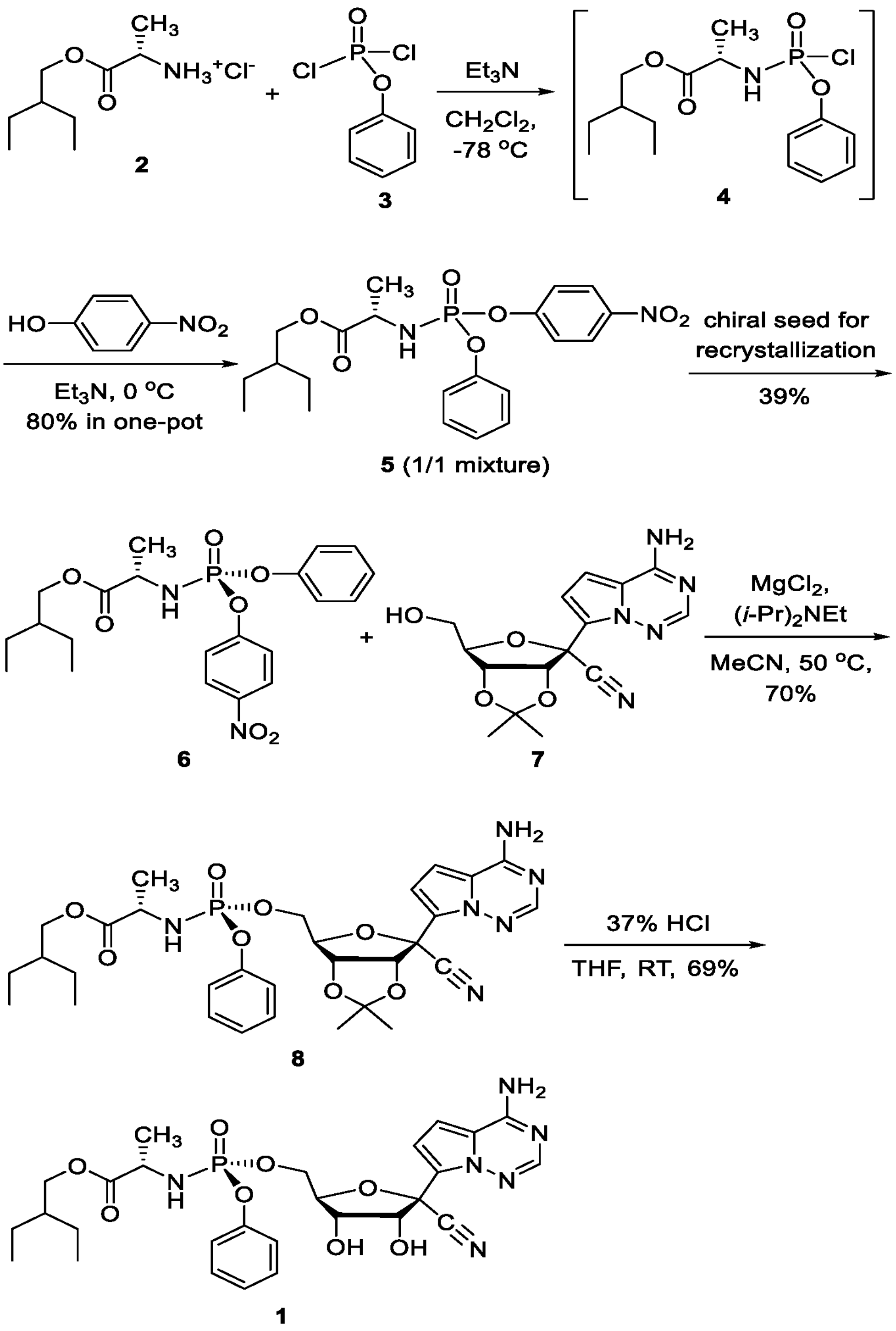
FIG. 2 is Gilead's scheme for the synthesis of remdesivir.

This invention relates to a novel process for the synthesis of the anti-coronavirus drug remdesivir (or GS-5734), in which chirality is introduced in the coupling reaction between phosphoramidoyl chloridate and D-ribose-derived 5-alcohol (i.e., compounds 4 and 7 in Gilead's scheme for the preparation of remdesivir as depicted in FIG. 2) via the use of a novel catalyst of this invention, thereby producing a diastereomerically enriched form of an intermediate (i.e., compound 8 in Gilead's scheme for the preparation of remdesivir as depicted in FIG. 2), which following acidic hydrolysis would give rise to the desired remdesivir. Accordingly, the present disclosure provides a novel catalyst and a new process for the preparation of remdesivir without the need to separate one of the enantiomers while minimizing the formation of undesired isomers, thus offers economic advantages for operation on a commercial scale.

Accordingly, it is the objective of the present disclosure to provide a one-pot synthetic process for the preparation of remdesivir (GS-5734). The process comprises steps of:

(a) diastereoselective coupling of compounds 4 and 7 in the presence of a catalyst of this invention, thereby forming compound 8 with at least 85% selectivity; and (b) subjecting the compound 8 to acidic cleavage to give the remdesivir;

4

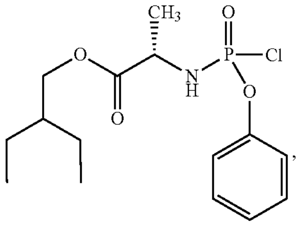

,

7

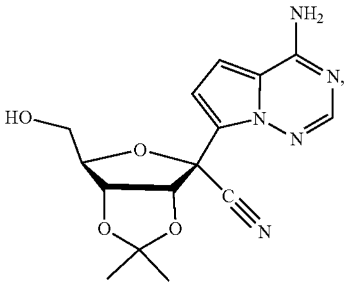

,

8

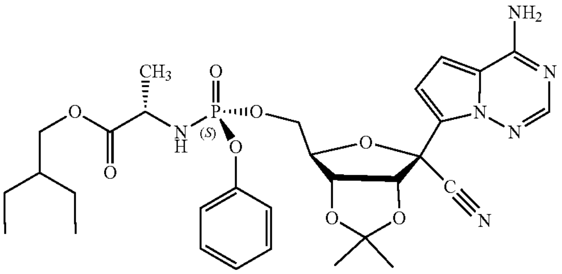

wherein, the compound 4 in the step (a) exists in a racemic mixture; and the steps (a) and (b) are performed in the same vessel without intermediate purification.

According to some embodiments of the present disclosure, the catalyst suitable for use in the step (a) has the structure of formula (1), (1)
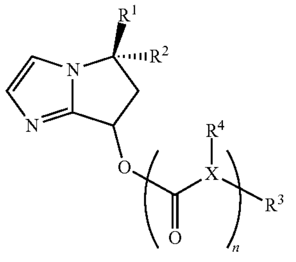
wherein,
- X is C or N;
- n is 0 or 1;
- $R^1$ and $R^2$ are independently hydrogen or phenyl;
- $R^3$ is tert-butyl, tert-butyldimethylsilyl (TBDMS), phenyl, benzyl, or adamantanyl; and
- $R^4$ is hydrogen provided that X is N, or $R^4$ is —$OCOCH_3$ provided that X is C. Examples of the catalyst of formula (1) suitable for use in the one-pot process include, but are not limited to,
26
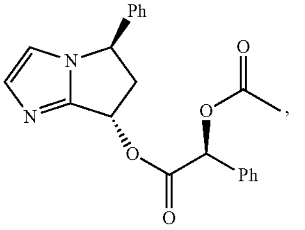
26A
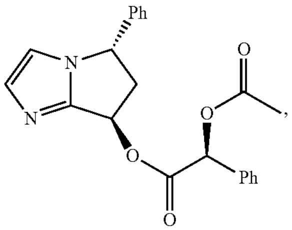
29
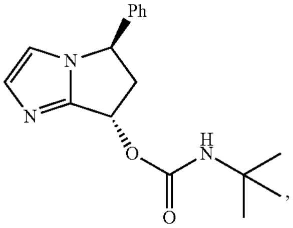
-continued
30
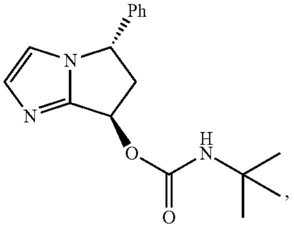
31
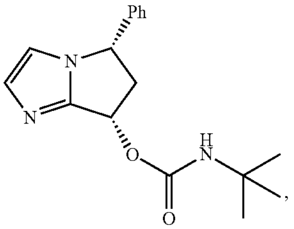
32
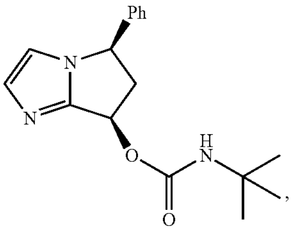
40
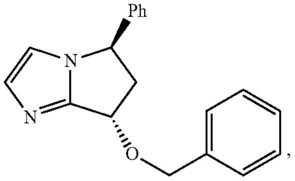
41
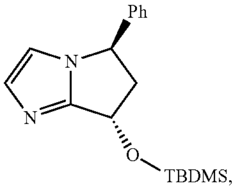
and -continued

42

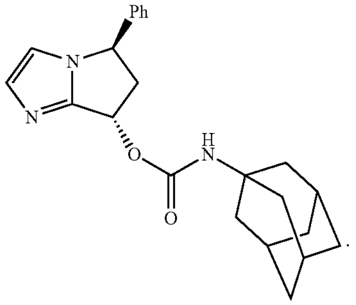

Preferably, the catalyst of formula (1) suitable for use in the one-pot process is compound 29.

According to other embodiments of the present disclosure, the catalyst suitable for use in the step (a) has the structure of formula (2-1)

(2-1)

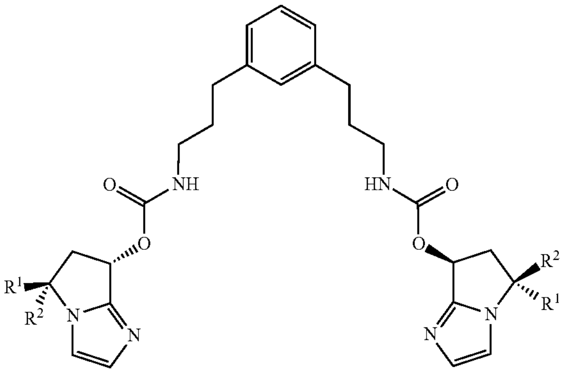

wherein, $R^1$ and $R^2$ are independently hydrogen or phenyl.

Examples of the catalyst of formula (2-1) suitable for use in the one-pot process include, but are not limited to,

34

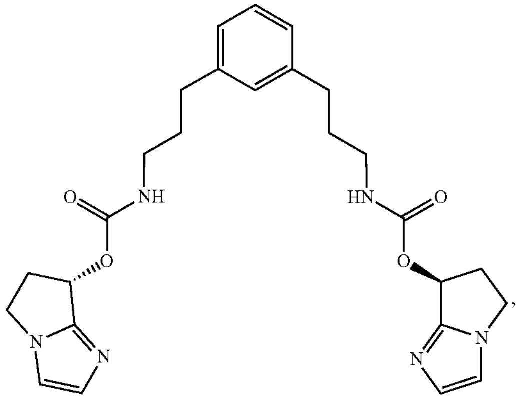

-continued

36

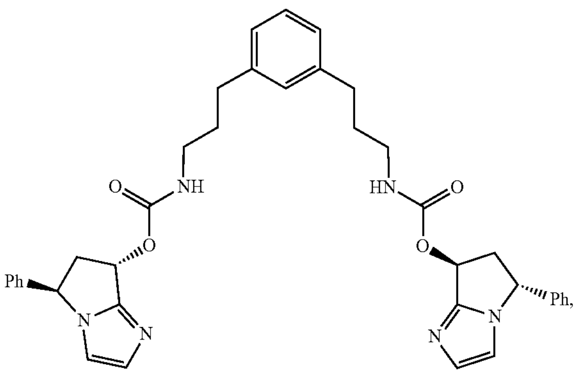

and

38

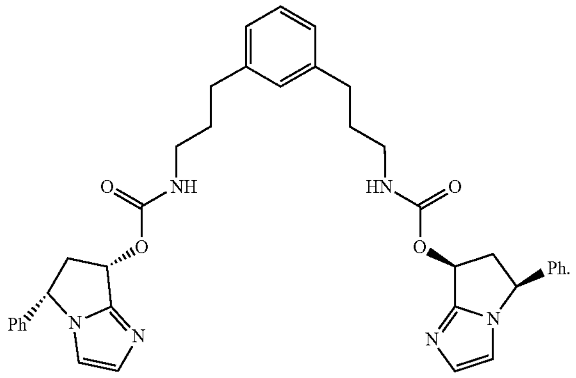

According to further embodiments of the present disclosure, the catalyst suitable for use in the step (a) has the structure of formula (2-2), (2-2)

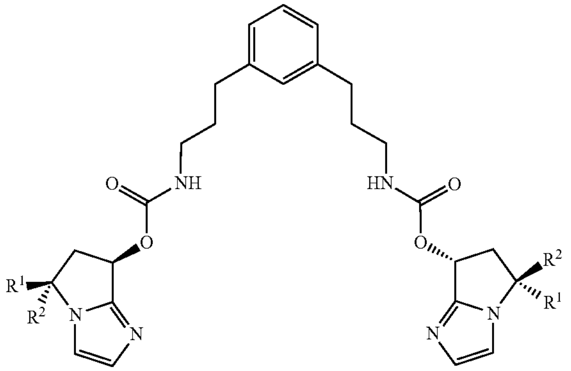

wherein, $R^1$ and $R^2$ are independently hydrogen or phenyl.

Examples of the catalyst of formula (2-1) suitable for use in the one-pot process include, but are not limited to,

37

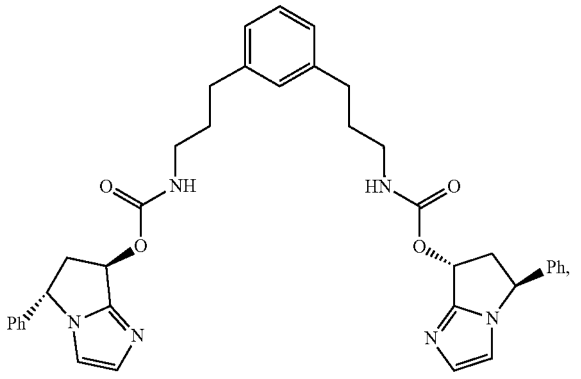

and

39

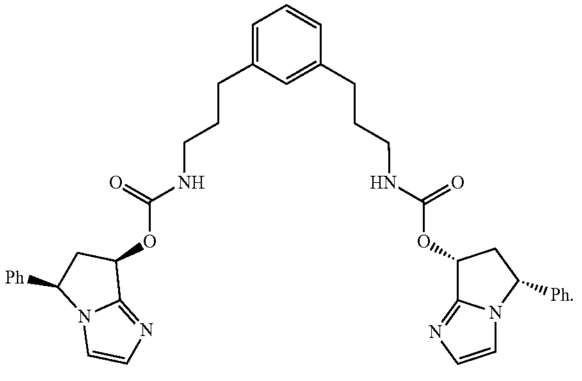

According to embodiments of the present disclosure, the catalyst in the step (a) may be present in the amount of 10-100 mol %, such as 10, 15, 20, 25, 30, 35, 40, 45, 50, 60, 65, 70, 75, 80, 85, 90, 95, and 100 mol %; preferably, the catalyst is present in the amount of 15-50 mol %, such as 15, 20, 25, 30, 35, 40, 45, and 50 mol %; most preferably, the catalyst is present in the amount of 20 mol %. Further, the step (a) is performed at a temperature between −10° C. to −50° C. for a period of 12 to 48 hrs.

According to preferred embodiments of the present disclosure, 20 mol % of the catalyst of formula (1), (2-1) or (2-2) are used to catalyze the coupling reaction between compounds 4 and 7, thereby producing compound 8 in (Sp)-diasetreomerically enriched form, in which the selectivity of (Sp)-diasetreomer over (Rp)-diasetreomer is at least 80%, such as 81, 82, 83, 84, 85, 86, 87, 88, 89, 90, 91, 92, 93, 94, 95, 96, 97, 98, and 99%; preferably, the selectivity of (Sp)-diasetreomer over (Rp)-diasetreomer is at least 90%, such as 90, 91, 92, 93, 94, 95, 96, 97, 98, and 99%; more preferably, at least 95%, such as 95, 96, 97, 98, and 99%. In one embodiment, compounds 4 and 7 are coupled in the presence of 20 mol % of compound 29 at −20° C. for 24 hr, thereby forming compound 8 with 96.1% selectivity (i.e., 96.1% of the product of the step (a) are (Sp)-diastereomers, while the rest of the product are (Rp)-diasetreomer) and 97% yield. In another embodiment, compounds 4 and 7 are coupled in the presence of 20 mol % of compound 31 at −20° C. for 24 hr, thereby forming compound 8 with 89% selectivity (i.e., 89% of the product of the step (a) are (Sp)-diastereomers, while the rest of the product are (Rp)-diasetreomer) and 79% yield. In a further embodiment, compounds 4 and 7 are coupled in the presence of 20 mol % of compound 34 at −20° C. for 24 hr, thereby forming compound 8 with 91.7% selectivity (i.e., 91.7% of the product of the step (a) are (Sp)-diastereomers, while the rest of the product are (Rp)-diasetreomer) and 94% yield. In still a further embodiment, compounds 4 and 7 are coupled in the presence of 20 mol % of compound 38 at −20° C. for 24 hr, thereby forming compound 8 with 84.5% selectivity (i.e., 84.5% of the product of the step (a) are (Sp)-diastereomers, while the rest of the product are (Rp)-diasetreomer) and 93% yield.

The compound 8 thus produced in the step (a) is then subjected to acidic hydrolysis to remove the isopropylidene protective group, thereby producing the desired remdesivir (step (b)). The acidic hydrolysis is conducted in a solution that comprises p-toluenesulfonic acid (p-TSA) and methanol at 40° C. for 6 hrs in the same reaction flask as that of step (a), thereby achieving one-pot synthesis of remdesivir. A typical one-pot synthesis for preparing remdesivir according to the present invention comprises the above mentioned steps (a) to (b), which are performed in the same reaction vessel without intermediate purification.

According to preferred embodiment of the present disclosure, the remdesivir thus produced in the step (b) may be further purified by any suitable means, such as column chromatography. In one specific embodiment, the yield of remdesivir after purification is 73%. In addition, the catalyst may be recycled or recovered as well. In certain embodiments, compound 29, which serves as the catalyst, is recovered at a yield of 82%.

The present invention is further illustrated by the following examples, which are provided by way of illustration only and should not be construed to limit the scope of the present invention.

EXAMPLES

Example 1 Preparation and Characterization of the Present Chiral Catalyst

In this example, for synthesis of remdesivir 1, series of chiral bicyclic imidazoles (compounds 26-32, and 42-45) and bis bicyclic imidazoles (compounds 33 to 41) serving as chiral catalysts were designed and synthesized to ensure compound 8 would acquire desired (S)-stereochemistry at the phosphorus center. The efficacy of each synthesized catalyst in achieving desired stereo-selectivity was also evaluated.

1.1 Synthesis of the Present Chiral Catalyst 1.1.1 Synthesis of Compounds 26 and 26A

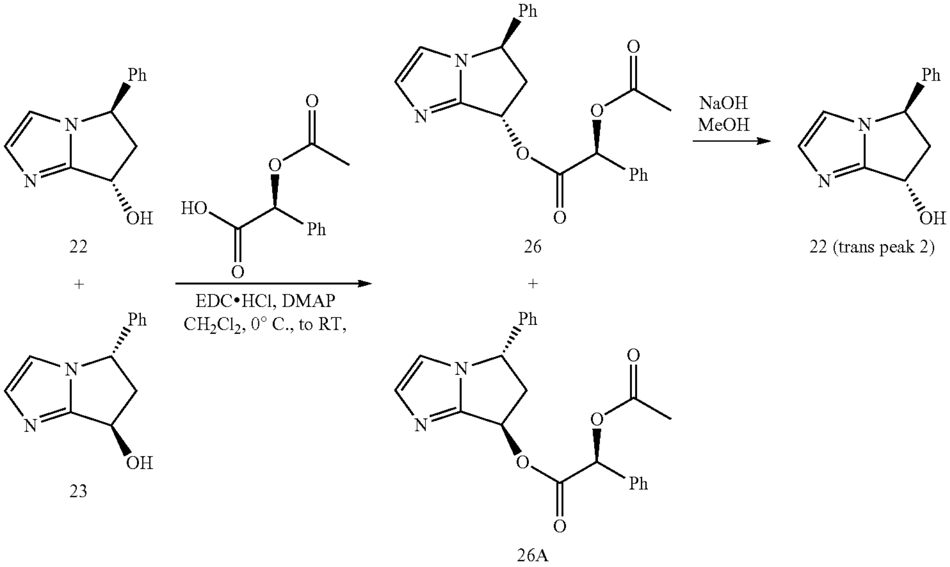 [SMILES: O[C@H]1C[C@H](c2ccccc2)n2ccnc21 ; CC(=O)O[C@H](C(=O)O)c1ccccc1 ; CC(=O)O[C@H](C(=O)O[C@H]1C[C@H](c2ccccc2)n2ccnc21)c1ccccc1 ; O[C@H]1C[C@H](c2ccccc2)n2ccnc21 ; O[C@@H]1C[C@@H](c2ccccc2)n2ccnc21 ; CC(=O)O[C@H](C(=O)O[C@@H]1C[C@@H](c2ccccc2)n2ccnc21)c1ccccc1]

22 + 23 → 26 + 26A → 22 (trans peak 2)

To a solution of trans-isomers (1.0 g, 4.99 mmol) and (+)-O-Acetyl-L-mandelic acid in $CH_2Cl_2$, added EDC·HCl (1.43 g, 7.40 mmol) and DMAP (0.61 g, 4.99 mmol) at 0° C. Then, the reaction temperature was gradually warmed up to room temperature and allowed to stir for 3 h. The TLC analysis indicated the complete conversion of starting materials into their respective products. The reaction mixture was concentrated and the crude residue was dissolved in ethyl acetate and washed with sat. $NaHCO_3$ solution. The organic layer was dried over $MgSO_4$, filtered, and concentrated in vacuo. The crude mixture was subjected to silica gel column chromotography by using ethyl acetate/hexane (1/3) as eluent to afford 26 (820 mg, 44%) as a semi solid and 26A (790 mg, 42%) as a gummy solid.

Compound 26.

$^1$H NMR (600 MHz, $CDCl_3$): δ 7.49 (d, J=4.3 Hz, 2H), 7.44-7.36 (m, 6H), 7.22 (s, 1H), 7.15 (d, J=6.7 Hz, 2H), 6.78 (d, J=0.6 Hz, 1H), 6.10 (d, J=6.5 Hz, 1H), (s, 1H), 5.47 (t, J=6.9 Hz, 1H), 3.11 (dd, J=14.7, 6.8 Hz, 1H), 2.91 (dt, J=13.9, 6.8 Hz, 1H), 2.23 (s, 3H).

$^{13}$C NMR (150 MHz, $CDCl_3$): δ 171.0, 168.8, 150.3, 139.3, 135.4, 133.0, 129.7, 129.4, 129.1, 128.9, 127.9, 126.5, 115.4, 75.0, 68.9, 59.6, 46.1, 20.9.

HRMS m/z (ESI, M+Na$^+$) calcd for $C_{12}H_{12}N_2ONa^+$ 399.1315, found 399.1330.

Compound 26 A.

$^1$H NMR (600 MHz, $CDCl_3$): δ 7.44 (dd, J=6.5, 2.9 Hz, 2H), 7.39-7.36 (m, 3H), 7.35-7.29 (m, 3H), 7.20 (s, 1H), 7.05-6.99 (m, 2H), 6.71 (d, J=0.6 Hz, 1H), 6.10 (dd, J=6.5, 1.8 Hz, 1H), 5.15 (t, J=6.9 Hz, 1H), 2.77 (dt, J=13.6, 6.7 Hz, 1H), 2.70 (ddd, J=14.7, 6.9, 1.8 Hz, 1H), 2.15 (s, 3H).

$^{13}$C NMR (150 MHz, $CDCl_3$): δ 170.3, 168.5, 150.4, 139.1, 135.5, 133.8, 129.6, 129.4, 129.1, 129.0, 128.0, 126.4, 115.4, 74.6, 68.7, 59.5, 45.9, 20.9.

HRMS m/z (ESI, M+Na$^+$) calcd for $C_{12}H_{12}N_2ONa^+$ 399.1315, found 399.1329.

1.1.2 General Procedure (A) for the Synthesis of Compounds 27 and 28.

To a solution of an alcohol (50 mg, 0.40 mmol) in THF (1.0 mL) was added sodium hydride (60% in mineral oil, 19 mg, 0.48 mmol) in portions. After 30 min, tert-butylisocyanate (40 mg, 0.40 mmol) was added dropwise. After 16 h the reaction was quenched by the addition of water (2.0 mL) and was then partitioned between water (2.0 mL) and iPAc (4.0 mL). The organic layer was washed with brine (4.0 mL), dried over $MgSO_4$, filtered and concentrated to yield a pale orange semi-solid. The residue was dissolved in MTBE (2.0 mL) with gentle heating, and then heptane (2.0 mL) was added over 10 min. After 2 h the mixture was filtered and washed with 1/1 MTBE/heptane (2 mL) and dried under nitrogen stream to yield desired compound.

Compound 27

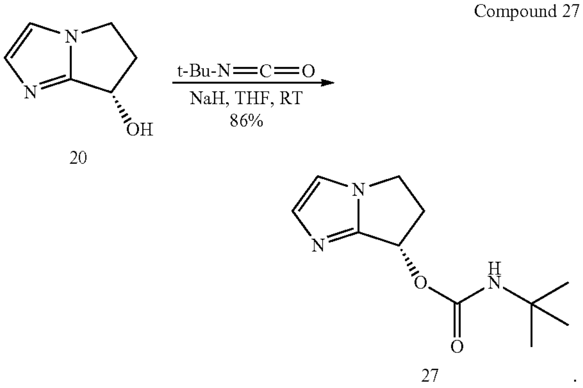

20 → 27.

Compound 27 was prepared according to the general procedure (A) as a white solid (77 mg, 86%).

$^1$H NMR (600 MHz, $CDCl_3$): δ 7.17 (s, 1H), 6.93 (s, 1H), 5.87 (d, J=4.8 Hz, 1H), 4.75 (s, 1H), 4.04-4.10 (m, 1H), 3.98-3.94 (m, 1H), 3.08-3.02 (m, 1H), 2.61-2.57 (m, 1H), 1.30 (s, 9H).

$^{13}C$ NMR (150 MHz, $CDCl_3$): δ 154.1, 151.8, 135.0, 115.6, 67.3, 50.7, 43.1, 35.6, 29.0.

HRMS m/z (ESI, M+H$^+$) calcd for $C_{11}H_{18}N_3O_2^+$ 224.1394, found 224.1398.

Compound 28

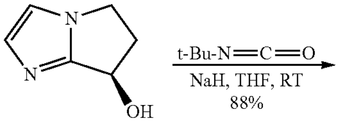

21

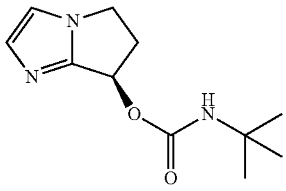

28

Compound 28 was prepared according to the general procedure (A) as a white solid (79 mg, 88%).

$^1H$ NMR (600 MHz, $CDCl_3$): δ 7.18 (s, 1H), 6.93 (s, 1H), 5.87 (d, J=5.4 Hz, 1H), 4.75 (s, 1H), 4.14-4.10 (m, 1H), 3.98-3.94 (m, 1H), 3.07-3.02 (m, 1H), 2.61-2.57 (m, 1H), 1.30 (s, 9H).

$^{13}C$ NMR (150 MHz, $CDCl_3$): δ 154.1, 151.8, 135.0, 115.6, 67.3, 50.8, 43.1, 35.6, 29.8, 29.0. HRMS m/z (ESI, M+H$^+$) calcd for $C_{11}H_{18}N_3O_2^+$ 224.1394, found 224.1398.

1.1.3 General Procedure (B) for the Synthesis of Compounds 29-32 and 42.

To a solution of alcohol (50 mg, 0.25 mmol) and tert-butylisocyanate (25 mg, 0.25 mmol) in THF, sodium hydride (60% in mineral oil, 7.2 mg, 0.30 mmol) was added at room temperature. After 30 min, the reaction was quenched by the addition of water (2 mL) and concentrated to give a pale orange semi-solid. The crude residue was purified by using silica gel column chromatography.

Compound 29

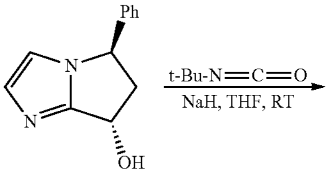

22

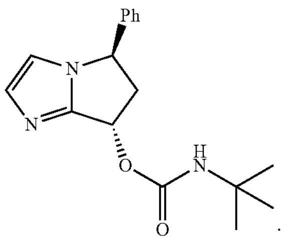

29

Compound 29 was prepared according to the general procedure (B) as a white solid (66 mg, 89%).

$^1H$ NMR (600 MHz, $CDCl_3$): δ 7.40-7.36 (m, 3H), 7.24 (s, 1H), 7.14 (d, J=6.1 Hz, 2H), 6.78 (s, 1H), 6.03 (d, J=5.7 Hz, 1H), 5.44 (t, J=6.0 Hz, 1H), 4.81 (s, 1H), 3.08-3.04 (m, 1H), 2.92-2.87 (m, 1H), 1.34 (s, 9H).

$^{13}C$ NMR (150 MHz, $CDCl_3$): δ 153.9, 151.8, 139.6, 135.1, 129.4, 128.8, 126.4, 115.1, 67.2, 59.6, 50.7, 46.6, 29.0.

HRMS m/z (ESI, M+H$^+$) calcd for $C_{17}H_{22}N_3O_2^+$ 300.1707, found 300.1712.

Compound 30

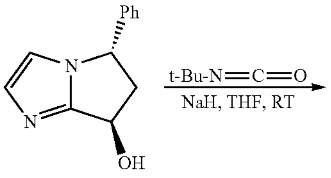

23

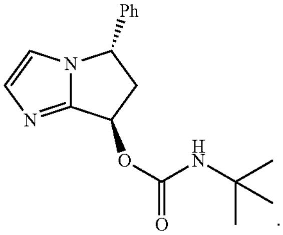

30

Compound 30 was prepared according to the general procedure (B) as a white solid (62 mg, 87%).

$^1H$ NMR (600 MHz, $CDCl_3$): δ 7.38-7.32 (m, 3H), 7.21 (s, 1H), 7.18 (d, J=6.0 Hz, 2H), 6.77 (s, 1H), 5.98-5.97 (m, 1H), 5.23-5.20 (m, 1H), 4.79 (s, 1H), 3.60-3.55 (m, 1H), 2.49-2.47 (m, 1H), 1.29 (s, 9H).

$^{13}C$ NMR (150 MHz, $CDCl_3$): δ 154.0, 151.8, 140.5, 135.4, 129.3, 128.7, 126.4, 115.0, 67.2, 59.3, 50.8, 45.7, 29.8, 29.0.

HRMS m/z (ESI, M+H$^+$) calcd for $C_{17}H_{22}N_3O_2^+$ 300.1707, found 300.1706.

Compound 31

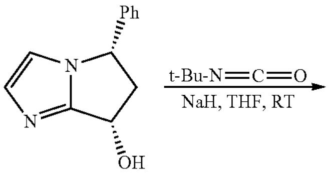

24

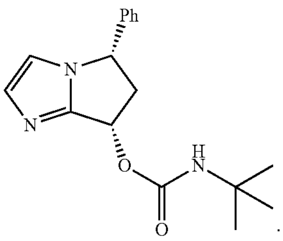

31

Compound 31 was prepared according to the general procedure (B) as a white solid (62 mg, 87%).

$^1H$ NMR (600 MHz, $CDCl_3$): δ 7.40-7.36 (m, 3H), 7.24 (s, 1H), 7.14 (d, J=6.0 Hz, 2H), 6.78 (s, 1H), 6.03 (d, J=5.2

Hz, 1H), 5.42 (t, J=6.0 Hz, 1H), 4.80 (s, 1H), 3.08-3.04 (m, 1H), 2.92-2.87 (m, 1H), 1.34 (s, 9H).

$^{13}$C NMR (150 MHz, $CDCl_3$): δ 153.96, 151.85, 139.70, 135.254, 129.36, 128.79, 126.37, 115.11, 67.23, 59.64, 50.78, 46.66, 29.02.

HRMS m/z (ESI, M+H$^+$) calcd for $C_{17}H_{22}N_3O_2^+$ 300.1707, found 300.1715.

Compound 32

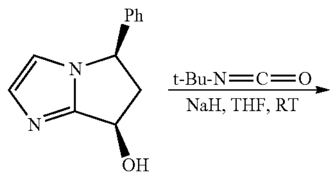

25

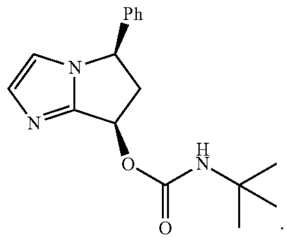

32

Compound 32 was prepared according to the general procedure (B) as a white solid (61 mg, 85%).

$^1$H NMR (600 MHz, $CDCl_3$): δ 7.38-7.33 (m, 3H), 7.26 (s, 1H), 7.21-7.17 (m, 2H), 6.77 (s, 1H), 5.97 (dd, J=12.2, 6.8 Hz, 1H), 5.21 (dd, J=12.0, 6.0 Hz, 1H), 4.78 (s, 1H), 3.59-3.56 (m, 1H), 2.48 (dd, J=12.0 Hz, 6.0 Hz, 1H), 1.30 (s, 9H).

$^{13}$C NMR (150 MHz, $CDCl_3$): δ 154.0, 151.8, 140.5, 135.4, 129.3, 128.7, 126.4, 115.0, 67.3, 59.3, 50.8, 45.7, 29.8, 29.0.

HRMS m/z (ESI, M+H$^+$) calcd for $C_{17}H_{22}N_3O_2^+$ 300.1707, found 300.1702.

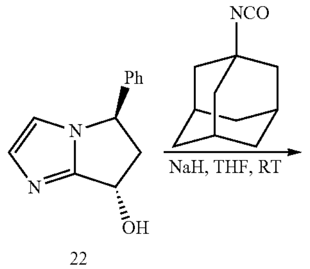

22

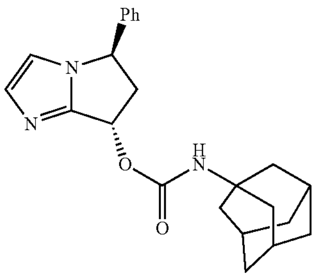

42

To a solution of alcohol (100 mg, 0.5 mmol) and 1-Adamantyl isocyanate (106 mg, 0.6 mmol) in THF, sodium hydride (60% in mineral oil, 24 mg, 1.0 mmol) was added at room temperature. After 30 min, the reaction was quenched by the addition of water (2 mL) and concentrated to give a pale orange semi-solid. The crude residue was subjected to silica gel column chromatography by using 30%-40% EtOAc in hexane to afford product as foamy solid (167 mg, 89%).

$^1$H NMR (600 MHz, $CDCl_3$): δ 7.38-7.32 (m, 3H), 7.22 (s, 1H), 7.11 (d, J=7.32 Hz, 2H), 6.75 (s, 1H), 5.97 (d, J=6.4 Hz, 2H), 5.4 (t, J=6.8 Hz, 1H), 4.66 (s, 1H), 3.05-3.02 (m, 1H), 2.88-2.83 (m, 1H), 2.07 (s, 3H), 1.92 (s, 6H), 1.66 (s, 6H).

$^{13}$C NMR (150 MHz, $CDCl_3$): δ 153.5, 151.9, 139.7, 135.3, 129.4, 128.8, 126.4, 115.1, 67.2, 59.6, 51.2, 46.6, 41.9, 36.5, 29.6.

1.1.4 General Procedure (C) for the Synthesis of Compounds 34-39.

4,4'-(1,3-Phenylene)dibutanoic acid (200 mg, 0.80 mmol) and triethylamine (0.25 mL, 1.80 mmol) were dissolved in THF (4.0 mL). After cooling to 0° C., ethyl chloroformate (0.17 mL, 1.80 mmol) was added dropwise and the mixture was stirred for min. To this mixture was added a solution of sodium azide (0.26 g, 4.0 mmol) in water (3.4 mL). After 30 min, toluene (10.0 mL) and water (10.0 mL) were added and the organic layer was separated. The aqueous layer was extracted with toluene (10.0 mL) and the combined organic layers were dried over $MgSO_4$, filtered, and concentrated to ~50% of the original volume. The crude solution of the acyl azide was then heated to 90° C. for min, then concentrated to yield the diisocyanate (195 mg, 90%) as yellow oil which was used in the next step without further purification. THF (4.0 mL) was added to dissolve the residue. Then, the corresponding starting material among (20-25) (1.6 mmol) was added followed by sodium hydride (60% suspension in mineral oil, 14 mg, 0.36 mmol). An additional portion of sodium hydride was added to complete the reaction. After 30 min, a few drops of water were added to quench the reaction and the solvent removed in vacuo. The crude residue was purified by silica gel chromatography by using ethyl acetate/hexane (3/1)

Compound 34

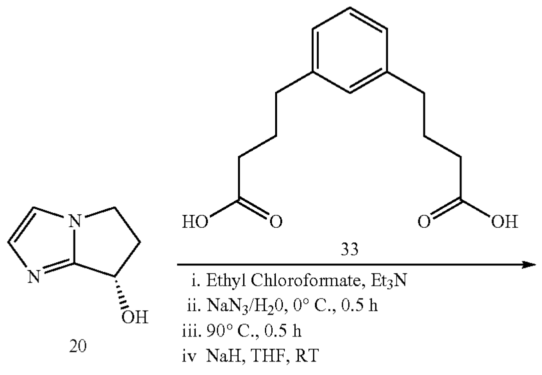

20

-continued

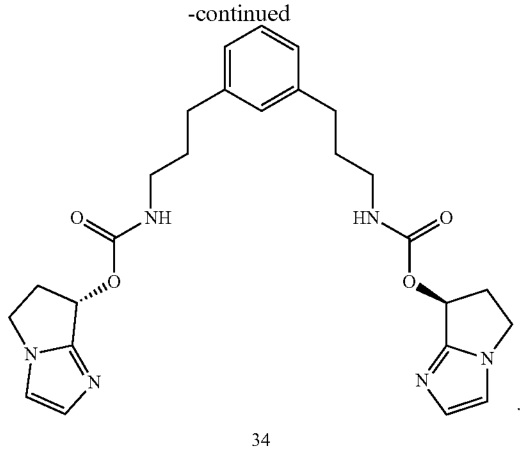

34

Compound 34 was prepared according to the general procedure (C) as a white solid (299 mg, 76%).

$^{1}H$ NMR (600 MHz, $CDCl_3$): δ 7.17-7.15 (m, 3H), 7.0-6.93 (m, 5H), 5.90-5.87 (m, 2H), 5.17-4.95 (m, 2H), 4.14-4.09 (m, 2H), 3.98-3.95 (m, 2H), 3.24-3.12 (m, 4H), 3.08-3.00 (m, 2H), 2.61-2.57 (m, 6H), 1.83-1.77 (m, 4H).

$^{13}C$ NMR (151 MHz, $CDCl_3$): δ 155.9, 151.7, 142.1, 141.6, 135.0, 134.8, 128.9, 128.8, 126.3, 126.3, 115.6, 67.9, 43.1, 40.7, 39.8, 35.5, 35.4, 33.1, 32.9, 31.9, 31.6, 31.4.

HRMS m/z (ESI, M+H$^{+}$) calcd for $C_{26}H_{33}N_6O_4^+$ 493.2558, found 493.2556.

Compound 35

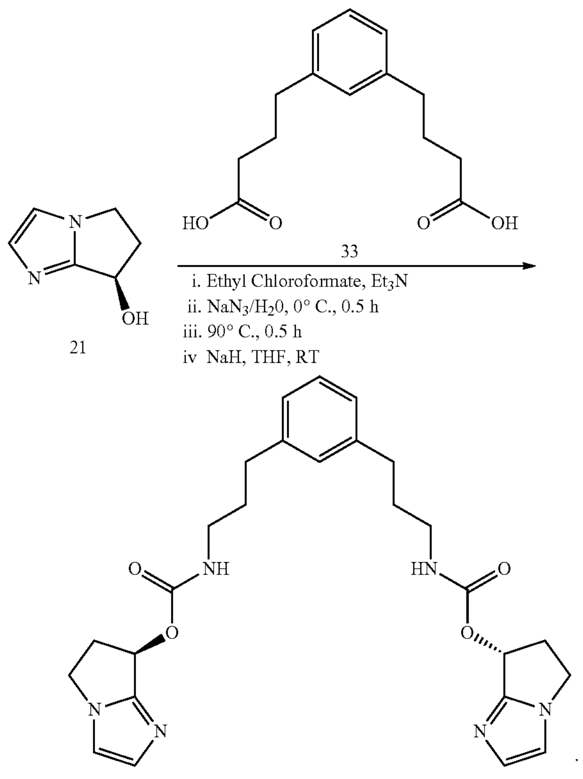

35

Compound 35 was prepared according to the general procedure (C) as a white solid (295 mg, 75%).

$^{1}H$ NMR (600 MHz, $CDCl_3$): δ 7.20-7.15 (m, 3H), 7.0-6.93 (m, 5H), 5.90-5.89 (m, 2H), 4.97 (bs, 2H), 4.14-4.10 (m, 2H), 3.98-3.94 (m, 2H), 3.25-3.13 (m, 2H), 3.08-3.02 (m, 2H), 2.62-2.57 (m, 6H), 1.84-1.77 (m, 4H).

$^{13}C$ NMR (150 MHz, $CDCl_3$): δ 155.9, 151.7, 141.6, 134.9, 128.8, 126.3, 115.6, 77.4, 77.2, 77.0, 67.9, 43.1, 40.7, 35.5, 33.1, 31.6.

HRMS m/z (ESI, M+H$^{+}$) calcd for $C_{26}H_{33}N_6O_4^+$ 493.2558, found 493.2556.

Compound 36

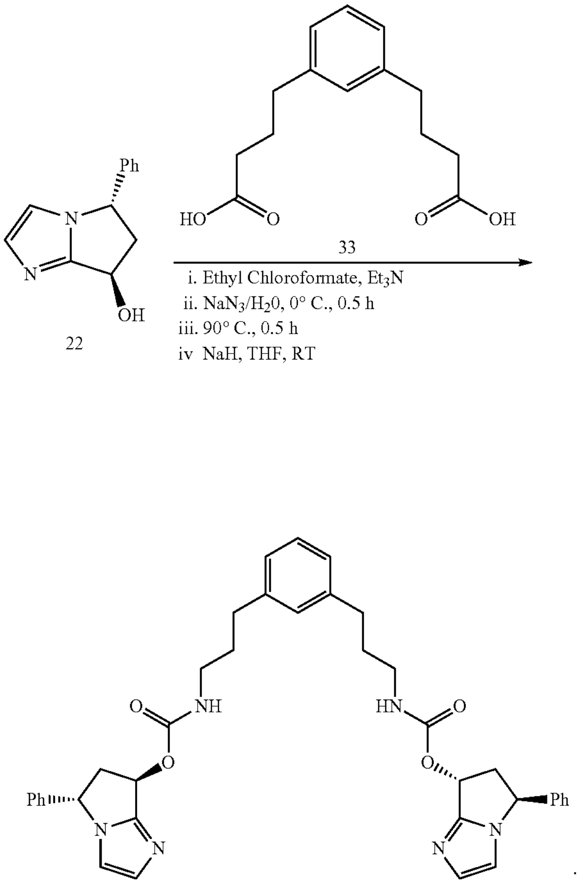

36

Compound 36 was prepared according to the general procedure (C) as a white solid (278 mg, 54%).

$^{1}H$ NMR (600 MHz, $CDCl_3$): δ 7.38-7.34 (m, 6H), 7.26 (bs, 2H), 7.11 (bs, 4H), 7.01 (bs, Hz, 3H), 6.74 (s, 2H), 6.02 (s, 2H), 5.40 (bs, 1H), 5.04 (bs, 2H), 3.20-3.18 (m, 4H), 3.05-3.02 (m, 2H), 2.89-2.85 (m, 2H), 2.62 (t, J=6.2 Hz, 4H), 2.47 (t, J=5.7 Hz, 4H).

$^{13}C$ NMR (150 MHz, $CDCl_3$): δ 155.8, 151.7, 141.7, 139.7, 135.3, 129.4, 128.8, 128.79, 128.7, 126.4, 126.3, 115.1, 67.9, 59.6, 46.6, 40.8, 33.1, 31.6.

HRMS m/z (ESI, M+H$^{+}$) calcd for $C_{26}H_{33}N_6O_4^+$ 645.3184, found 645.3173.

Compound 37

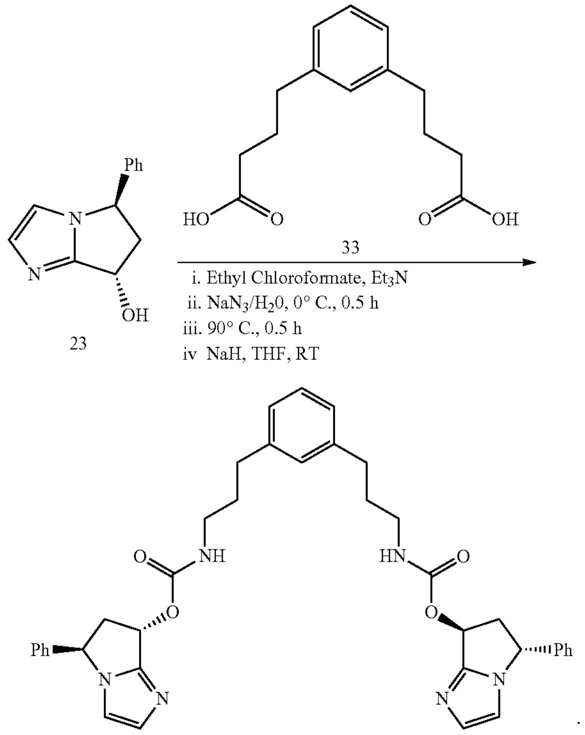

23

33

37

Compound 37 was prepared according to the general procedure (C) as a white solid (288 mg, 56%).

$^1$H NMR (600 MHz, $CDCl_3$): δ 7.38-7.34 (m, 6H), 7.26 (d, J=5.9 Hz, 2H), 7.11 (d, J=6.0 Hz, 4H), 7.01 (d, J=6.0 Hz, 4H), 6.75 (s, 1H), 6.02 (d, J=5.2 Hz, 2H), (t, J=6.1 Hz, 2H), 4.94 (bs, 2H), 3.25-3.18 (m, 4H), 3.05-3.02 (m, 2H), 2.89-2.85 (m, 2H), 2.62 (t, J=6.2 Hz, 4H), 2.47 (t, J=5.7 Hz, 4H).

$^{13}$C NMR (150 MHz, $CDCl_3$): δ 155.8, 151.7, 141.7, 139.7, 135.3, 129.4, 128.8, 128.8, 128.7, 126.4, 126.3, 115.1, 67.9, 59.6, 46.6, 40.8, 33.1, 31.6.

HRMS m/z (ESI, M+H$^+$) calcd for $C_{26}H_{33}N_6O_4^+$ 645.3184, found 645.3177.

Compound 38

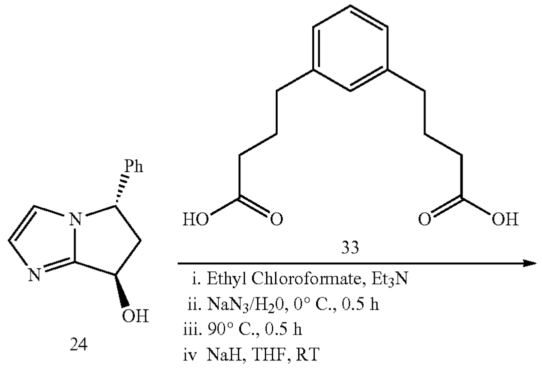

24

33

-continued

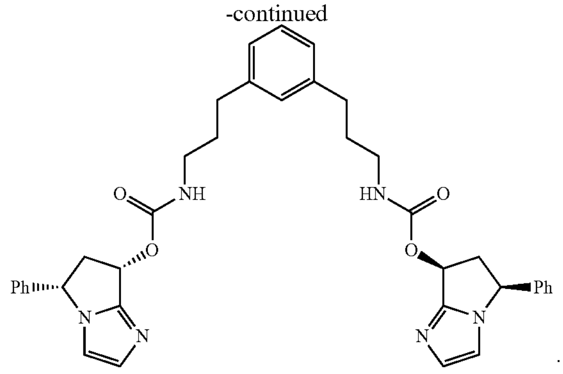

38

Compound 38 was prepared according to the general procedure (C) as a white solid (293 mg, 57%).

$^1$H NMR (600 MHz, $CDCl_3$): δ 7.34-7.33 (m, 6H), 7.25 (s, 2H), 7.20-7.15 (m, 5H), 6.96 (bs, 3H), 6.77 (s, 2H), 5.99 (s, 2H), 5.20 (s, 2H), 4.98 (s, 2H), 3.56-3.55 (m, 2H), 3.20-3.14 (m, 4H) 2.58-2.47 (m, 6H), 1.8 (bs, 4H).

$^{13}$C NMR (150 MHz, $CDCl_3$): δ 155.8, 151.7, 141.7, 139.7, 135.2, 129.4, 128.8, 128.8, 126.4, 126.2, 115.1, 67.8, 59.6, 46.5, 40.8, 33.1, 31.6.

HRMS m/z (ESI, M+H$^+$) calcd for $C_{26}H_{33}N_6O_4^+$ 645.3184, found 645.3190.

Compound 39

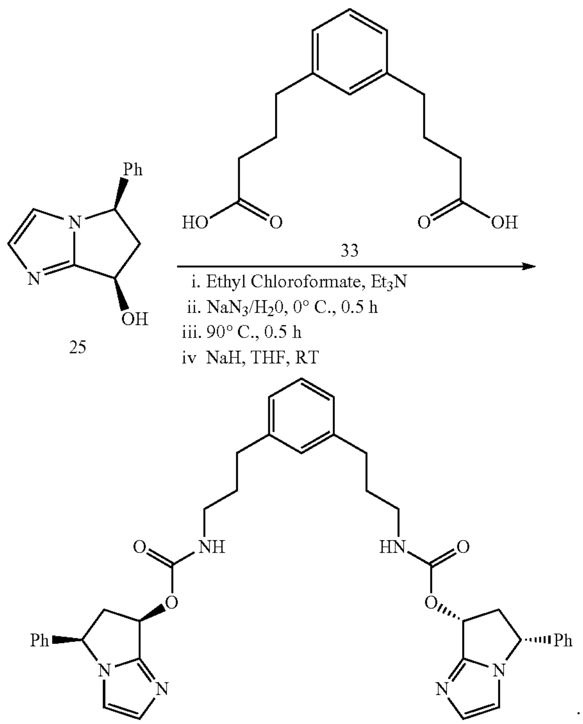

25

33

39

Compound 39 was prepared according to the general procedure (C) as a white solid (283 mg, 55%).

$^1$H NMR (600 MHz, $CDCl_3$): δ 7.34-7.33 (m, 6H), 7.25 (s, 2H), 7.20-7.15 (m, 5H), 6.96 (bs, 3H), 6.77 (s, 2H), 5.99 (s, 2H), 5.20 (s, 2H), 4.98 (s, 2H), 3.56-3.55 (m, 2H), 3.20-3.14 (m, 4H) 2.58-2.47 (m, 6H), 1.8 (bs, 4H).

$^{13}C$ NMR (150 MHz, $CDCl_3$): δ 155.8, 151.7, 141.7, 139.7, 135.2, 129.4, 128.8, 128.8, 126.4, 126.3, 115.1, 67.9, 59.6, 46.5, 40.8, 33.1, 31.6.

HRMS m/z (ESI, $M+H^+$) calcd for $C_{26}H_{33}N_6O_4^+$ 645.3184, found 645.3176.

1.1.5 Synthesis of Compounds 40-41

Compound 40

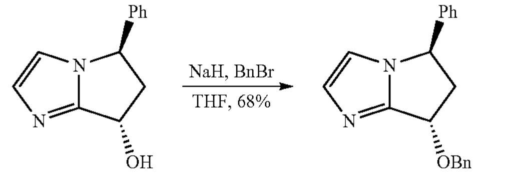

22 40 .

To a solution of alcohol 22 (100 mg, 0.51 mmol) and benzyl chloride (104 mg, mmol) in anhydrous DMF (2.0 mL), NaH (9.0 mg, 0.37 mmol) was added. The reaction mixture was allowed to stir at room temperature under $N_2$, and the progress of the reaction was monitored by TLC. After 8 h, the TLC analysis indicates the complete conversion of starting materials into products. The reaction mixture was quenched with ice-cold water and extracted with EtOAc, organic layers were dried over $MgSO_4$, filtered, and concentrated in vacuo. The crude residue was subjected to silica gel column chromatography to afford benzyl ether 40 (99 mg, 68%) as a colorless oil.

$^1H$ NMR (600 MHz, $CDCl_3$): δ 7.41-7.34 (m, 7H), 7.30-7.27 (m, 1H), 7.20 (s, 1H), 7.15-7.13 (s, 2H), 6.74 (s, 1H), 5.46 (dd, J=12.0, 6.0 Hz, 1H), 4.95-4.90 (m, 2H), 4.75-4.73 (m, 1H), 3.06-3.02 (m, 1H), 2.73-2.69 (m, 1H).

$^{13}C$ NMR (150 MHz, $CDCl_3$): δ 153.6, 139.9, 138.0, 134.2, 129.3, 128.7, 128.6, 128.3, 127.9, 126.6, 114.7, 71.5, 71.0, 59.9, 47.0, 29.9.

HRMS m/z (ESI, $M+H^+$) calcd for $C_{19}H_{19}N_2O^+$ 291.1492, found 291.1493.

Compound 41

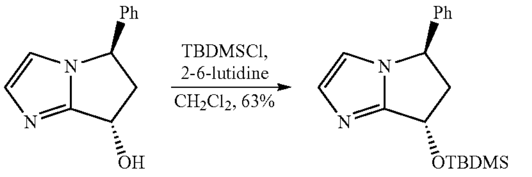

22 41 .

To a solution of alcohol 22 (100 mg, 0.51 mmol) and 2,6-lutidine (80.4 mg, 0.75 mmol) in $CH_2Cl_2$ (1.5 mL) was added tert-butyldimethylsilyl chloride (TBDMSCl) (0.11 mL, 0.5 mmol) at 0° C. The mixture was warmed to room temperature and allowed to stir for 12 h. After concentration in vacuo, the residue was subjected to silica gel chromatography by using ethyl acetate in hexane (0→100%) as an eluent to afford desired compound 41 as a colorless liquid (99 mg, 63%).

$^1H$ NMR (600 MHz, $CDCl_3$): δ 7.36-7.33 (m, 3H), 7.17 (s, 1H), 7.10 (s, 2H), 6.67 (s, 1H), 5.44 (s, 1H), 5.21 (s, 1H), 2.88-2.86 (m, 1H), 2.71-2.68 (m, 1H), 0.92 (s, 9H), 0.22 (s, 3H), 0.13 (s, 3H). $^{13}C$ NMR (150 MHz, $CDCl_3$): δ 155.2, 140.4, 134.4, 129.3, 128.6, 126.5, 114.2, 66.3, 59.4, 49.8, 26.1, 18.5, −4.3, −4.6.

HRMS m/z (ESI, $M+H^+$) calcd for $C_{18}H_{27}N_2OSi^+$ 315.1887, found 315.1889.

1.2 Characterization of the Catalyst of Example 1.1

In this example, the catalyst prepared in Example 1.1 was used to catalyze the coupling reaction between 1:1 phosphoramidoyl chloridates 4 with the D-ribose-derived 7, thereby forming compounds 8 and 8a. The selectivity and yield of the products 8 and 8a are summarized in Table 1.

1.2.1 General Procedure for the Catalytic Asymmetric Phosphoramidation

Scheme 1

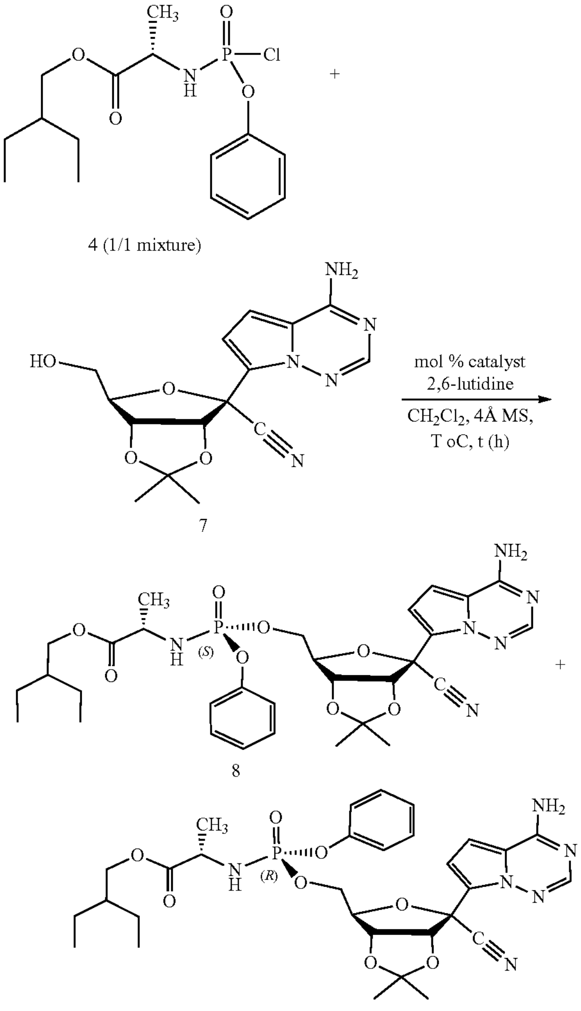

4 (1/1 mixture)

7

8

8a

In a flame dried round bottom flask, a mixture of acetonide-nucleoside acceptor 7 (10.0 mg, 0.03 mmol) and catalyst (mol % was according to Table 1 below) were co-evaporated with anhydrous toluene (1.0 mL, 2 times), dried for 2 h on high-vacuum. The mixture was dissolved in dry $CH_2Cl_2$ (1.0 mL) and then freshly activated 4 Å molecular sieves (20 mg) followed by 2,6-luditine (7.0 μL, 0.06 mmol) were added. The suspension was then stirred under $N_2$ atmosphere at room temperature for 10 min, and then cooled to −20° C. After 10 min, a solution of phosphochloridate 4 (15.7 mg, 0.05 mmol) in dry $CH_2Cl_2$ (0.5 mL) was added and the reaction mixture was allowed to stir at same temperature for 24 h. TLC analysis indicates the complete conversion of starting materials into the products. The whole reaction mixture was filtered through a pad of Celite®, the filtrate was concentrated in vacuo. The crude residue was dissolved in MeOH and filtered off. The filtrate was subjected to HPLC analysis.

TABLE 1

The results of chiral catalysts of Example 1.1 for stereoselective coupling of compounds 4 and 7.

| Entry | Catalyst | Mol % | T (° C.) | t (h) | Yield (%) | Ratio of 8/8a[a] |
|---|---|---|---|---|---|---|
| 1 | 27 | 20 | −20 | 24 | 94% | 93.6/6.4 |
| 2 | 28 | 20 | −20 | 24 | 64% | 65.4/34.6 |
| 3 | 29 | 20 | −20 | 24 | 97% | 96.1/3.9 |
| 4 | 30 | 20 | −20 | 24 | 65% | 55.4/44.6 |
| 5 | 31 | 20 | −20 | 24 | 79% | 89.0/11.0 |
| 6 | 32 | 20 | −20 | 24 | 42% | 49.0/51.0 |
| 7 | 34 | 20 | −20 | 24 | 94% | 91.7/8.3 |
| 8 | 35 | 20 | −20 | 24 | 88% | 12.7/87.3 |
| 9 | 36 | 20 | −20 | 24 | 96% | 96.1/3.9 |
| 10 | 37 | 20 | −20 | 24 | 96% | 28.1/71.9 |
| 11 | 38 | 20 | −20 | 24 | 93% | 84.5/15.5 |
| 12 | 39 | 20 | −20 | 24 | 92% | 14.7/85.3 |
| 13 | 40 | 20 | −20 | 24 | 68% | 83.1/16.9 |
| 14 | 41 | 20 | −20 | 24 | 61% | 80.3/19.7 |
| 15 | 42 | 20 | −40 | 48 | 86% | 96.8/3.2 |
| 16 | 26 | 20 | −20 | 24 | 67% | 75.1/24.9 |
| 17 | 29 | 20 | −10 | 24 | 90% | 94.5/5.5 |
| 18 | 29 | 20 | −40 | 48 | 92% | 96.8/3.2 |
| 19 | 29 | 20 | −78 | 48 | 0% | 0/0 |
| 20 | 29 | 2 | −20 | 55 | 79% | 81.6/18.4 |
| 21 | 29 | 10 | −20 | 24 | 64% | 86.1/13.9 |
| 22 | 29 | 15 | −20 | 30 | 93% | 95.8/4.2 |
| 23 | 29 | 50 | −20 | 12 | 93% | 97.1/2.9 |
| 24 | 29 | 50 | −40 | 24 | 95% | 97.3/2.7 |
| 25 | 29 | 100 | −40 | 24 | 95% | 97.7/2.3 |

[a]The ratio was determined by HPLC analysis.

Referring to Table 1, in entry 1, when 20 mol % of the (S)-carbamate 27 was used in the reaction at −20° C. for 24 h, a mixture of the diastereomers 8 and 8a was obtained in 94% yield with a ratio of 93.6/6.4 (determined by HPLC). In contrast, the (R)-carbamate 28 gave 64% yield with a 65.4/34.6 ratio (entry 2). Obviously, the (S)-configuration of 27 favored the formation of (S)-P-diastereomer in both selectivity and yield. We then tested the (S)-carbamate 29 having an extra phenyl group with (R)-configuration under similar conditions (entry 3), and the ratio (96.1/3.9) and yield (97%) were slightly increased in comparison with 27. On the other hand, in entry 5, when the (S)-carbamate 31 attaching an extra (S)-phenyl group was tested, a decrease of the yield (79%) and ratio (89.0/11.0) was observed. The configuration of this extra phenyl group is important for the asymmetric phosphoramidation. We next individually examined the (R)-carbamates 30 [entry 4, (9-Ph] and 32 [entry 6, (R)-Ph], and similar results were found as compared to 28 (entry 2).

Regarding the catalysts of bis-bicyclic imidazoles, the ratios of 8/8a were generated in 91.7/8.3 (entry 7, 94% yield), 96.1/3.9 (entry 9, 96% yield) and 84.5/15.5 (entry 11, 93% yield) by using the dimeric (S)-carbamates 34, 36, and 38, respectively. Interestingly, the dimeric (R)-carbamates 35 (entry 8), 37 (entry 10) and 39 (entry 12) furnished the undesired diastereomer 8a as a major product in much better yields and ratios in comparison with the monomeric (R)-carbamates 28, 30 and 32, respectively. In addition to the carbamate moiety, the (S)-benzyl ether (40, entry 13), (S)-silyl ether (41, entry 14), (S)-adamantyl carbamate (42, entry 15), and (S)-ester (26, entry 16) were further carried out to provide the 8/8a rations in 83.1/16.9 (68%), 80.3/19.7 (61%), 96.8/3.2 (86%) and 75.1/24.9 (67%), respectively.

Since compound 29 provides the best results in the catalyst screening in terms of yield and selectivity, thus, its catalytic properties as well as temperature effect were further investigated. It was found that when the reaction was carried out at −10° C. (entry 17), the yield (90%) and selectivity (94.5/5.5) slightly decreased. Whereas, at a lower temperature −40° C., marginal improvement of the selectivity (96.8/3.2) was observed (entry 18). However, the reaction time required 48 h for completion due to the decrease of catalytic activity. Moreover, no reaction was initiated at −78° C. (entry 19). In entries 19-24, various catalytic concentrations were studied. Reducing the amounts of catalyst 29 to mol % (entry 22), 10 mol % (entry 21) and 2 mol % (entry 20), both selectivity and yield gradually decreased. When 50 mol % of 29 was checked at −20° C. (entry 23), the selectivity slightly increased from 96.1/3.9 to 97.1/2.9 and the reaction was completed in 12 h. By lowering temperature to −40° C. (entry 24), a ratio of 97.3/2.7 was obtained. Similar phenomenon was observed by employing 100 mol % of 29 (entry 25), providing a 97.7/2.3 ratio.

Example 2 One-Pot Synthesis of Remdesivir

One-pot synthesis of remdesivir 1 was carried out in accordance with steps described in Scheme 2, in which all reactions were carried out in the same flask without intermediate purification until the final product (i.e., remdesivir) was produced. Remdesivir was produced in 73% yield after C18 column purification. The catalyst 29 was recovered in 82% yield.

Scheme 2

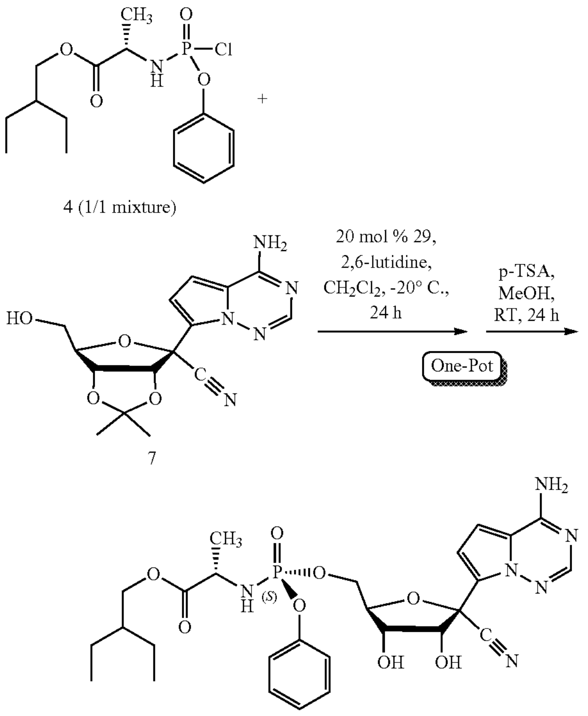

4 (1/1 mixture)

7

1

In a flame dried round bottom flask, a mixture of acetonide-nucleoside acceptor 7 (1.0 g, 3.02 mmol) and catalyst 29 (180 mg, 0.62 mmol) were co-evaporated with anhydrous toluene (20 mL, 2 times), dried for 2 h on high-vacuum. The mixture was dissolved in dry $CH_2Cl_2$ (50 mL) and then freshly activated 4 Å molecular sieves (1.5 g) followed by 2,6-luditine (700 μL, 6.04 mmol) were added. The suspension was then stirred under $N_2$ atmosphere at room temperature for 10 min, and then cooled to −20° C. After 10 min, a solution of phosphochloridate 4 (1.57 g, 4.53 mmol) in dry $CH_2Cl_2$ (5 mL) was added and the reaction mixture was allowed to stir at same temperature for 24 h. TLC analysis indicates the complete conversion of starting materials into the products. Then the $CH_2Cl_2$ was evaporated by vacuum. Later on, the crude material was treated with 10.0 equiv of p-TSA in MeOH (50 mL). The reaction mixture was allowed to stir for 24 h at room temperature and the TLC analysis indicated the product formation. Then the reaction mixture was filtered through a pad of Celite® to remove 4 Å molecular sieves, quenched by adding $Et_3N$ and concentrated in vacuo. The crude residue was dissolved in EtOAc and washed with Saturated $NaHCO_3$, the aqueous layer was back extracted with EtOAc (3×50 mL) and the combined organic layers were dried over $MgSO_4$, filtered and concentrated in vacuo. The crude residue was subjected to silica gel column chromatography by using EtOAc in hexane (0→100%) as an eluent to afford the products as a foamy solid. The diastereomeric mixture was purified by using C18 column to give compound 1 as a foamy solid (1.39 g, 73%).

$^1H$ NMR (600 MHz, $CD_3OD$) δ 7.87 (s, 1H), 7.30 (t, J=7.8 Hz, 2H), 7.21-7.14 (m, 3H), 6.91 (d, J=4.6 Hz, 1H), 6.88 (d, J=4.6 Hz, 1H), 4.79 (d, J=5.4 Hz, 1H), 4.42-4.35 (m, 2H), 4.28 (dt, J=10.5, 5.1 Hz, 1H), 4.17 (t, J=5.6 Hz, 1H), 4.02 (dd, J=5.8 Hz, 1H), 3.90 (ddd, J=23.7, 12.7, 6.4 Hz, 2H), 1.45 (dt, J=12.3, 6.2 Hz, 1H), 1.34-1.28 (m, 7H), 0.85 (t, J=7.5 Hz, 6H).

$^{13}C$ NMR (150 MHz, $CD_3OD$) δ 175.15, 175.1, 157.4, 152.3, 152.3, 148.4, 130.9, 126.2, 125.7, 121.51, 121.5, 118.1, 117.7, 112.5, 102.8, 84.44, 81.4, 84.4, 75.9, 71.8, 68.2, 67.3, 67.27, 41.8, 24.4, 24.3, 20.7, 20.6, 11.5, 11.4.

In conclusion, this invention provides an efficient catalyst for stereoselective (S)-P-phosphoramidation in excellent yield and selectivity. The 1/1 racemic mixture of phosphoramidoyl chloridates 4 may be directly used as the coupling reagent for the synthesis of remdesivir, avoiding a waste of the other diastereomer. In addition, a high yielding combination of (S)-P-phosphoramidation and isopropylidene-deprotection successfully provided remdesivir in a one-pot manner. The catalyst may be recovered in good yield, and similar results were obtained with the recycled catalyst. Accordingly, this one-pot cost-down process has a potential being scale-up for industrial production.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A catalyst that is any one of,

26

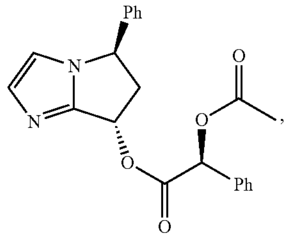,

26A

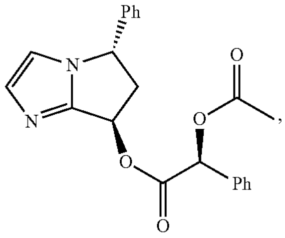,

29

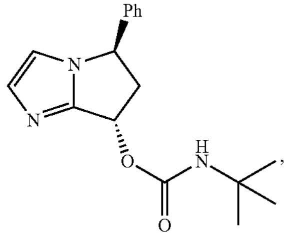,

31

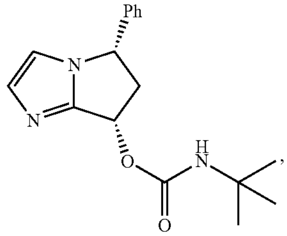,

40

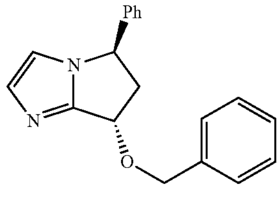,

41

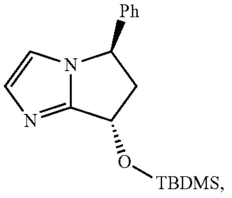 or

-continued
42
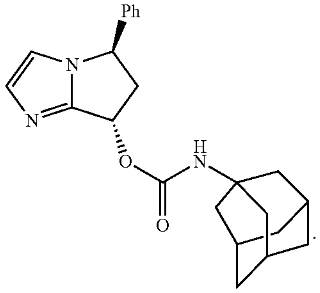
* * * * *